United States Patent [19]

Rigamonti et al.

[11] Patent Number: 4,992,585

[45] Date of Patent: Feb. 12, 1991

[54] PROCESS FOR PRODUCING α-CHLOROACETOACETIC ACID MONOMETHYLAMIDE

[75] Inventors: Flaviano Rigamonti, Monthey, Switzerland; Pullissery Raghunandan, Goa, India

[73] Assignee: Ciba-Geigy Corporation, Ardsley, N.Y.

[21] Appl. No.: 421,572

[22] Filed: Oct. 16, 1989

Related U.S. Application Data

[63] Continuation-in-part of Ser. No. 350,991, May 12, 1989, abandoned, which is a continuation of Ser. No. 924,382, Oct. 29, 1986, abandoned, which is a continuation-in-part of Ser. No. 738,914, May 29, 1985, abandoned.

[30] Foreign Application Priority Data

May 29, 1984 [CH] Switzerland .................... 2636/84-0

[51] Int. Cl.$^5$ .................. C07C 235/80; C07C 231/24
[52] U.S. Cl. .................................................. 564/199
[58] Field of Search ........................................ 564/199

[56] References Cited

U.S. PATENT DOCUMENTS

| | | | |
|---|---|---|---|
| 3,483,252 | 12/1969 | Beriger | 564/199 |
| 3,917,694 | 11/1975 | Reinink | 564/199 |
| 4,207,259 | 6/1980 | Kunstle et al. | 564/199 |
| 4,235,818 | 11/1980 | Dousse et al. | 564/199 |

*Primary Examiner*—Carolyn S. Elmore
*Attorney, Agent, or Firm*—Kevin T. Mansfield

[57] ABSTRACT

In the production of α-chloroacetoacetic acid monomethylamide by reaction of chlorine with acetoacetic acid monomethylamide in an aqueous medium at temperature of −20 to +10° C. in the presence of urea and alkali metal salts, neutralization of the reaction mixture, separation of solid α-chloroacetoacetic acid monomethylamide and feeding back of the mother liquor into the next batch, yield and purity of the product are improved by extracting the mother liquor obtained each time after the separation of α-chloroacetoacetic acid monomethylamide, before the mother liquor is fed back into the next batch, with an inert solvent immiscible with water.

8 Claims, No Drawings

PROCESS FOR PRODUCING α-CHLOROACETOACETIC ACID MONOMETHYLAMIDE

This is a continuation-in-part of Ser. No. 350,991 filed May 12, 1989, abandoned, which is a continuation of Ser. No. 924,382, filed Oct. 29, 1986, abandoned, which is a continuation-in-part of Ser. No. 738,914 filed May 29, 1985, abandoned.

The present invention relates to a process for producing α-chloroacetoacetic acid monomethylamide by chlorination of acetoacetic acid monomethylamide in an aqueous medium.

α-Chloroacetoacetic acid monomethylamide is a valuable intermediate for producing insecticidal active substances. It produces for example, on reaction with trimethyl-phosphite, O,O-dimethyl-O-(1-methyl-2-methylcarbamoylvinyl) phosphate, which has become known, under the name of monocrotophos, as an active ingredient in insecticidal compositions.

In the production of α-chloroacetoacetic acid monomethylamide by chlorination of acetoacetic acid monomethylmide in an aqueous medium and separation of the product in solid form, there arise essentially two problems. The one lies in the fact that, on account of the high reactivity of the α-methylene group of the acetoacetic acid monomethylamide, both hydrogen atoms in the α-position are readily replaced by chlorine. The other is caused by solubility of α-chloroacetoacetic acid monomethylamide in water, which renders more difficult to complete separation of the product from the aqueous reaction medium.

It has been suggested to overcome these difficulties in the preparation of α-chloroacetoacetic acid amides by a process which comprises reacting the corresponding acetoacetic acid amides at low temperature in an aqueous reaction medium containing water as the sole solvent with chlorine, separating the α-chloroacetoacetic acid amide formed from the reaction mixture by an exhaustive extraction with a water-immiscible solvent and recovering the product from the extract by evaporation of the solvent (cf. U.S. Pat. No. 4,207,259). Depending on the molar ratio of chlorine to acetoacetic acid amide the product obtained is 95.5–97.4% pure and contains 2.0–2.5% by weight of unreacted starting material and 0.6–1.5% by weight of α,α-dichlorinated product. While this process is satisfactory with respect to yield and purity of the product it is complicated and uneconomical in view of the large amount of organic solvent used in the extraction and its removal from the extract by distillation.

Further, it has already been suggested that the α,α-dichlorination be avoided by performing chlorination at low temperatures in the presence of urea and with the use of less than the stoichiometric amount of chlorine (cf. U.S. Pat. Nos. 3,483,252 and 4,235,818). Attempts have been made to keep the losses in yield, resulting from the high water-solubility of α-chloroacetoacetic acid monomethylamide, to a low level by feeding in each case 50–85% of the mother liquor obtained after separation of solid α-chloroacetoacetic acid monomethylamide back into the next batch (cf. U.S. Pat. No. 4,235,818).

The results attainable with the partial feed back of the mother liquor from the preceding batch are however not fully satisfactory with regard to technical, economical and ecological aspects. The by-products formed in the process, such as α,α-dichloroacetoacetic acid monomethylamide, dichloroacetic acid monomethylamide and tarry products accumulate with each further recycling step and thus deteriorate product quality. For example, when the process is carried out with a recyclisation of 80% of the mother liquor obtained each time after separation of solid α-chloroacetoacetic acid monomethylamide a steady state is reached after several recyclisations. In this steady state of the process a yield of about 67%–71% of theory of α-chloroacetoaetic acid monomethylamide is obtained in each batch calculated on the amount of freshly added acetoacetic acid monomethylamide and the purity of the product is only about 83%. The remainder of the mother liquor, in which are contained acetoacetic acid monomethylamide (about 3% by weight) and α-chloroacetoacetic acid monomethylamide (about 4% by weight) is in each case lost and thus contaminates the environment.

It is therefore the object of the present invention to overcome these disadvantages and to provide a process which would enable α-chloroacetoacetic acid monomethylamide, of high quality to be produced to the greatest possible degree without losses and in the most favourable manner with respect to the environment.

In order to attain this object, there is suggested according to the invention a method of producing α-chloroacetoacetic acid monomethylamide by reaction of chlorine with acetoacetic acid monomethylamide in an aqueous medium, at temperatures of $-20°$ to $+10°$ C., in the presence of urea and alkali metal salts, neutralisation of the reaction mixture, separation of solid α-chloroacetoacetic acid monomethylamide, and feeding back of the mother liquor into the chlorination reaction, the procedure being such that the mother liquor obtained each time after the separation of α-chloroacetoacetic acid monomethylamide is extracted, before being recycled, with 2–10% by weight of an inert solvent immiscible with water, relative to the total amount of mother liquor.

Suitable solvents for the extraction of the mother liquor are aliphatic and aromatic hydrocarbons, such as hexane, heptane, cyclohexane, benzene toluene and xylene; also halogenated aliphatic and aromatic hydrocarbons, such as methylene chloride, chloroform, carbon tetrachloride, 1,2-dichloroethane, chlorobenzene and o-dichlorobenzene. Particularly favourable solvents are 1,2-dichloroethane and toluene.

The extraction can be carried out either batchwise, in a single stage or in several steps, in a vessel with stirrers, or continuously in extraction columns having 1–10 preferably 3–5, theoretical separation stages. In the case of the continuous procedure, it is possible to separate according to both the co-current and the counter-current principle. On a account of the corrosive properties of the mother liquor, it is advantageous to use apparatus made from glass, enamel or high-alloy steels, for example Hastelloy C. For the single-stage extraction in a vessel with stirrer, there is preferably used 4–6% by weight of solvent, and for the multistage extraction preferably 3–5% by weight, relative to the total amount of mother liquor to be extracted. Extraction can be performed in the temperature range of $-20°$ to $50°$ C., and takes 15 minutes to 2 hours. The extraction is preferably carried out at $0°$–$20°$ C.

After extraction, the mother liquor can be recycled, without further purification, directly into the chlorination process. The solvent used for extraction can be recovered from the extract by distillation and can be re-used. The distillation residue contains, besides α,α-dichloroacetoacetic acid monomethylamide and acetoacetic acid monomethylamide, also α-chloroacetoacetic acid monomethylamide. These substances can be recovered from the distillation residue by fractional crystallisation from toluene or 1,2-dichloroethane. The α-chloroacetoacetic acid monomethylamide contained in the distillation residue is obtained in this manner to the extent of 50–70%.

The extraction of the mother liquor in the manner according to the invention enables, in contrast to the known process, the recyclisation of the whole of the mother liquor. The losses occurring in the production of α-chloroacetoacetic acid monomethylamide can thus be reduced to a minimum. At the same time, the α-chloroacetoacetic acid monomethylamide is obtained with a higher level of purity and in better yield compared with the corresponding results obtainable with the known process. By virtue of the fact that the whole of the mother liquor can be recycled, it is quite possible, in order to avoid the formation of α,α-dichloroacetoacetic acid monomethylamide, the use less than the equivalent amount of chlorine, for example 0.75–0.90 mol of chlorine per mol of acetoacetic acid monomethylamide, without unreacted acetoacetic acid monomethylamide being lost with the part of the mother liquor which is not recycled, in the way it is lost in the known process. This overall advantageous result of the process according to the invention has to be considered surprising, for it was not to be expected with the extraction of the mother liquor with the aforementioned solvents that the by-products contained in the mother liquor, which by-products can adversely affect the yield and product quality, could be selectively removed.

With the extraction of the mother liquor according to the present invention the composition of the extracted mother liquor remains unchanged and a practically infinite number of recyclisation can be carried out with the total amount of extracted mother liquor. Due to the lower contents of impurities of the extracted mother liquor as compared with the unextracted mother liquor of the old process the yield of α-chloroacetoacetic acid monomethylamide obtained in each batch is increased to about 75% of theory calculated on the amount of freshly added acetoacetic acid monomethylamide while, at the same time, the purity of the product is increased to about 91%.

The process according to the invention is further illustrated by the following Examples.

EXAMPLE 1

Production of α-chloroacetoacetic acid monomethylamide with recycling of mother liquor without extraction (prior art)

Into a vessel with stirrer are placed 1560 kg of a 50% aqueous solution of acetoacetic acid monomethylamide (780 kg of acetoacetic acid monomethylamide; 6.76 kmols), 78 kg of 1,2-dichloroethane, 181 kg of water, 206 kg of sodium chloride, 131 kg of urea and 6045 kg of mother liquor from the preceding batch, the liquor containing:

15% by weight of sodium chloride,
8% by weight of urea,
3% by weight of acetoacetic acid monomethylamide,
4% by weight of α-chloroacetoacetic acid monomethylamide,
3% by weight of by products, especially α,α-dichloroacetoacetic acid monomethylamide,
3.5% by weight of ammonium chloride,
2% by weight of 1,2-dichloroethane, and
61.5% by weight of water.

Into this mixture are then introduced below the surface, at −16° C. to −17° C., 475 kg (6.7 kmols) of chlorine. The pH value of the reaction mixture is subsequently adjusted at −6° C. to 6.5–6.8 by the addition of 114 kg of ammonia, and the precipitated α-chloroacetoacetic acid monomethylamide is separated by centrifuging. There are thus obtained 814 kg of α-chloroacetoacetic acid monomethylamide (83%; 67% of theory) and 7502 kg of mother liquor, of which 80% (6045 kg) is fed back into the next reaction. The remainder of the mother liquor is discarded.

EXAMPLE 2

Production of α-chloroacetoacetic acid monomethylamide with recycling of extracted mother liquor (process according to the present invention)

(a) Extraction of the mother liquor 8405 kg of mother liquor of the following composition:
16% by weight of sodium chloride,
8% by weight of urea,
3% by weight of acetoacetic acid monomethylamide,
4% by weight of α-chloroacetoacetic acid monomethylamide,
3% by weight of α,α-dichloroacetoacetic acid monomethylamide,
3.5% by weight of ammonium chloride,
1% by weight of dichloroacetic acid monomethylamide,
2% by weight of 1,2-dichloroethane, and
59.5% by weight of water are mixed in a vessel with stirrer, by vigorous stirring for one hour at room temperature, with 450 kg of 1,2-dichloroethane. Stirring is then discontinued and the layers are separated. After separation of the layers the composition of the aqueous layer is as follows:
17.2% by weight of sodium chloride,
8.5% by weight of urea,
2.4% by weight of acetoacetic acid monomethylamide,
3.0% by weight of α-chloroacetoacetic acid monomethylamide,
0.04% by weight of α,α-dichloroacetoacetic acid monomethylamide,
0.2% by weight of dichloroacetic acid monomethylamide,
3.7% by weight of ammonium chloride,
1.4% by weight of 1,2-dichloroethane, and
63.5% by weight of water.

(b) Recycling of the extracted mother liquor

Into a vessel with stirrer are placed 960 kg of an 85% aqueous solution of acetoacetic acid monomethylamide (technical grade 95.6% pure corresponding to 780 kg of acetoacetic acid monomethylamide; 6.76 kmols), 25 kg of urea, 104 kg of 1,2-dichloroethane and 8320 kg of the mother liquor obtained according to (a). Into this mixture are then introduced below the surface, at −16° C. to −17° C., 520 kg (7.33 kmols) of chlorine. The pH value of the reaction mixture is subsequently adjusted at −6° C. to 6.5–6.8 by the addition of 125 kg of ammonia, and the precipitated α-chloroacetoacetic acid monomethylamide is separated by centrifuging. There are thus obtained 839 kg of α-chloroacetoacetic acid monomethylamide (91%; 75% of theory, relative to freshly employed acetoacetic acid monomethylamide) and 8577 kg of mother liquor, which after extraction with 1,2-dichloroethane, is fed back into the next batch.

EXAMPLE 3

Production of α-chloroacetoacetic acid monomethylamide with recycling of mother liquor without extraction (prior art)

Into a vessel with stirrer are placed 1450 kg of a 50% aqueous solution of acetoacetic acid monomethylamide (725 kg of acetoacetic acid monomethylamide; 6.30 kmols), 32 kg of 1,2-dichloroethane, 236 kg of water, 184 kg of sodium chloride, 127 kg of urea, and 6333 kg of mother liquor from the preceding batch, the liquor containing:
- 11.5% by weight of sodium chloride,
- 8% by weight of urea,
- 3% by weight of acetoacetic acid monomethylamide,
- 3% by weight of α-chloroacetoacetic acid monomethylamide,
- 3% by weight of by products, especially α,α-dichloroacetoacetic acid monomethylamide and dichloroacetic acid monomethylamide,
- 9.5% by weight of ammonium chloride,
- 2% by weight of 1,2-dichloroethane, and
- 60% by weight of water.

Into this mixture are then introduced below the surface, at −16° C. to −17° C., 447 kg (6.3 kmols) of chlorine. The pH value of the reaction mixture is subsequently adjusted at −6° C. to 6.5–6.8 by the addition of 107 kg of ammonia, and the precipitated α-chloroacetoacetic acid monomethylamide is separated by centrifuging. There are thus obtained 814 kg of α-chloroacetoacetic acid monomethylamide (83%; 71% of theory), 186 kg solid ammonium chloride and 7916 kg of mother liquor, of which 80% (6333 kg) is fed back into the next reaction. The remainder of the mother liquor is discarded.

EXAMPLE 4

Production of α-chloroacetoacetic acid monomethylamide with recycling of extracted mother liquor (process according to the present invention)

(a) Extraction of the mother liquor 8340 kg of mother liquor of the following composition:
- 11.5% by weight of sodium chloride,
- 8% by weight of urea,
- 3% by weight of acetoacetic acid monomethylamide,
- 3% by weight of α-chloroacetoacetic acid monomethylamide,
- 2% by weight of α,α-dichloroacetoacetic acid monomethylamide,
- 9.5% by weight of ammonium chloride,
- 1% by weight of dichloroacetic acid monomethylamide,
- 2% by weight of 1,2-dichloroethane, and
- 60% by weight of water are mixed in a vessel with stirrer, by vigorous stirring for one hour at room temperature, with 450 kg of 1,2-dichloroethane. Stirring is then discontinued and the layers are separated. After separation of the layers the composition of the aqueous layer is as follows:
- 12.2% by weight of sodium chloride,
- 8.4% by weight of acetoacetic acid monomethylamide,
- 2.5% by weight of α-chloroacetoacetic acid monomethylamide,
- 0.04% by weight of α,α-dichloroacetoacetic acid monomethylamide,
- 0.2% by weight of dichloroacetic acid monomethylamide,
- 10.0% by weight of ammonium chloride,
- 0.5% by weight of 1,2-dichloroethane, and
- 63.4% by weight of water.

From the aqueous layer (8020 kg) 137 kg of water and 40 kg of residual 1,2-dichloroethane is distilled off under reduced pressure.

(b) Recycling of the extracted mother liquor

Into a vessel with stirrer are placed 915 kg of an 85% aqueous solution of acetoacetic acid monomethylamide (778 kg of acetoacetic acid monomethylamide; 6.76 kmols), 168 kg of 1,2-dichloroethane and 7843 kg of the mother liquor obtained according to (a). Into this mixture are then introduced below the surface, at −16° C. to −17° C., 520 kg (7.33 kmols) of chlorine. The pH value of the reaction mixture is subsequently adjusted at −6° C. to 6.5-6.8 by the addition of 125 kg of ammonia, and the precipitated α-chloroacetoacetic acid monomethylamide is separated by centrifuging. There are thus obtained 839 kg of α-chloroacetoacetic acid monomethylamide (91%; 75% of theory, relative to freshly employed acetoacetic acid monomethylamide), 392 kg of solid ammonium chloride and 8340 kg of mother liquor which, after extraction with 1,2-dichloroethane, is fed back into the next batch.

What is claimed is:

1. A process for producing α-chloroacetic acid monomethylamide which comprises the steps of
    reacting chlorine with acetoacetic acid monomethylamide in an aqueous medium, at a temperature of −20° to +10° C., in the presence of urea and an alkali metal salt,
    neutralizing the reaction mixture,
    separating solid α-chloroacetoacetic acid from the mother liquor, and
    recycling said mother liquor into a subsequent chlorination reaction of acetoacetic acid monomethyl amide,
    wherein all of said mother liquor, obtained each time after the separation of α-chloroacetoacetic acid monomethylamide, is extracted, before being recycled, with 2–10% by weight of an aliphatic or aromatic hydrocarbon or a halogenated aliphatic or aromatic hydrocarbon, relative to the total amount of mother liquor
    and then all of said extracted mother liquor is recycled into said subsequent chlorination reaction.

2. A process according to claim 1, wherein the solvent is selected from the group consisting of hexane, heptane, cyclohexane, benzene, toluene, xylene, methylene chloride, chloroform, carbon tetrachloride, 1,2-dichloroethane, chlorobenzene and o-dichlorobenzene.

3. A process according to claim 2, wherein the solvent is toluene or 1,2-dichloroethane.

4. A process according to claim 1, wherein there is used, for a single-stage extraction, 4–6% by weight of solvent, relative to the total amount of the mother liquor to be extracted.

5. A process according to claim 1, wherein there is used, for a multistage extraction 4–5% by weight of solvent, relative to the total amount of mother liquor to be extracted.

6. A process according to claim 1, wherein the extraction is performed in the temperature range of −20° to 50° C.

7. A process according to claim 1, wherein the extraction is performed at 0°–20° C.

8. A process according to claim 4, wherein the inert solvent is 1,2-dichloroethane.

* * * * *